United States Patent [19]

Pfingstl et al.

[11] Patent Number: 5,571,483
[45] Date of Patent: Nov. 5, 1996

[54] SYSTEM OF CONVERTING ENVIRONMENTALLY POLLUTANT WASTE GASES TO A USEFUL PRODUCT

[75] Inventors: Hans Pfingstl, East Amherst; Walter Martyniuk, Williamsville, both of N.Y.; Armand Ladage, Hennepin, Ill.; Tom McNally, Spring Valley, Ill.; Robert Myers, Hennepin, Ill.; Ludwig Eberle, Kempten, Germany

[73] Assignees: Exolon-ESK Company, Tonawanda, N.Y.; Electroschmelzwerk Kempten GmbH, Kempten, Germany

[21] Appl. No.: 470,923

[22] Filed: Jan. 26, 1990

[51] Int. Cl.⁶ .................................................. B01J 19/00
[52] U.S. Cl. .................... 422/166; 422/186.04; 422/187; 422/188
[58] Field of Search ................................. 422/129, 166, 422/186.04, 187, 188, 189; 568/888; 518/707, 713

[56] References Cited

U.S. PATENT DOCUMENTS

| | | |
|---|---|---|
| 3,378,446 | 4/1968 | Whittlesey . |
| 3,489,645 | 1/1970 | Daiber et al. . |
| 3,624,239 | 11/1971 | Fraas . |
| 3,762,992 | 10/1973 | Hedstrom . |
| 3,917,797 | 11/1975 | Reed et al. . |
| 3,928,973 | 12/1975 | Hand . |
| 3,950,602 | 4/1976 | Korsten et al. . |
| 3,976,829 | 8/1976 | Wiebke et al. . |
| 3,989,883 | 11/1976 | Wiebke et al. . |
| 4,053,544 | 10/1977 | Moore . |
| 4,061,716 | 12/1977 | McGauley . |
| 4,132,727 | 1/1979 | Gomberg ........................... 204/157.61 |
| 4,158,744 | 6/1979 | Petersen et al. . |
| 4,226,795 | 10/1980 | Bowman . |
| 4,339,546 | 7/1982 | Randalls ................................ 422/199 |
| 4,374,288 | 2/1983 | Scragg ................................... 422/199 |
| 4,399,546 | 8/1983 | Phillips . |
| 4,425,317 | 1/1984 | Zeller et al. . |
| 4,430,444 | 2/1984 | Reichl ..................................... 422/189 |
| 4,559,207 | 12/1985 | Hiller et al. ........................... 422/197 |
| 4,702,900 | 10/1987 | Kurachi et al. . |
| 4,744,869 | 5/1988 | Saito et al. . |
| 4,772,634 | 9/1988 | Farooque ................................ 422/189 |
| 4,836,993 | 6/1989 | Bertolacini et al. . |
| 4,946,477 | 8/1990 | Perka et al. . |
| 4,981,668 | 1/1991 | Dosaj et al. ........................... 568/888 |

FOREIGN PATENT DOCUMENTS

| | | |
|---|---|---|
| 0078591 | 5/1983 | European Pat. Off. . |
| 2512316 | 7/1976 | Germany . |
| 2809082 | 11/1978 | Germany . |
| 3515250 | 10/1986 | Germany . |

OTHER PUBLICATIONS

G. Vogt et al, "Novel RF-Plasma System for the Synthesis of Ultrafine, Ultrapure SiC and $Si_3N_4$", Mat. Res. Soc. Symp. Proc., vol. 30, pp. 283–289 (1984).

A. Kuibira et al, "Preparation of SiC and $Si_3N_4$ Powders by RF-plasma", J. Ceram. Soc. of Jpn., Inter. Ed., vol. 95, pp. 83–85. (1987).

J. O'Neil et al, "Production of Fine Ceramic Powders from Chloromethylslanes Using Pulsed Excimer RAdiation", J. Am. Ceram. Soc. 72[7], pp. 1130–1135 (1989).

K. Sawano, "Formation of SiC Powder from Laser Heated Vapor Phase Reactions" Abstract of article appearing at J. Ceram. Soc. of Jpn. 95 (1987).

Primary Examiner—Timothy M. McMahon
Attorney, Agent, or Firm—Hodgson Russ Andrews Woods & Goodyear

[57] ABSTRACT

A continuous flow method and system is provided for converting environmentally pollutant by-product waste gases emitted during the manufacture of a product in a first manufacturing plant to a useful product in a second manufacturing plant such that release of the gases into the atmosphere may be prevented.

19 Claims, 5 Drawing Sheets 5,571,483

SYSTEM OF CONVERTING ENVIRONMENTALLY POLLUTANT WASTE GASES TO A USEFUL PRODUCT

FIELD OF THE INVENTION

This invention relates generally to a system and method of converting environmentally pollutant gases such as hydrogen sulfide and carbon monoxide emitted during a manufacturing process such as the manufacture of silicon carbide in order to achieve a beneficial use of the gases as well as to prevent their evolution into the atmosphere.

BACKGROUND OF THE INVENTION

Industrial silicon carbide is generally produced by a discontinuous or batch process in a furnace typically of the electrical resistance type. Silicon carbide production is important because silicon carbide is considered a strategic stockpiled material by the government. The process generally involves mixing raw materials of silica, sand and petroleum coke and placing these materials in an electric resistance furnace. The reaction is then carried out by direct electrical heating. As a result of the process, various by-product waste gases consisting primarily of carbon monoxide, carbon dioxide and hydrogen are produced in large amounts. Other by-product waste gases, such as hydrogen sulfide and hydrocarbons such as methane also form from the impurities in the coke.

U.S. Pat. No. 3,976,829 discloses a gas collection system developed in the late 1970's for use with an electrical resistance furnace of the type disclosed in U.S. Pat. No. 3,950,602, 3,989,883 and 4,158,744. The gas collection system allows collection of the by-product waste gases during the manufacture of silicon carbide for subsequent incineration. During incineration the gases are converted into carbon dioxide and sulfur dioxide and then emitted into the atmosphere.

However, carbon dioxide and sulfur dioxide are pollutant gases, and emission thereof into the atmosphere is regulated for health and environmental reasons. In this connection, evolution of sulfur dioxide into the atmosphere is presently scrutinized in connection with the "acid-rain" effect. Many processes are available for removing the sulfurous contaminants from the gases. But these processes generally are costly in capital investment and wasteful in energy conservation. Furthermore, evolution of carbon dioxide into the atmosphere is presently scrutinized in connection with the "green-house" effect. Therefore, an economical system and method of converting environmentally pollutant by-product waste gases, such as hydrogen sulfide and carbon monoxide emitted during the manufacture of silicon carbide, whereby evolution of the gases into the atmosphere may be prevented would be desirable. Furthermore, the storage of the by-product gases for later use in a manufacturing process requires uneconomical storage handling steps. Therefore, it is desirable, to avoid storage while advantageously converting the by-product waste gases into useful products wherein they are not disadvantageously emitted to the atmosphere.

SUMMARY AND OBJECTS OF THE INVENTION

Accordingly, it is an object of the present invention to prevent emission into the atmosphere of pollutant by-product waste gases produced during the manufacture of product such as silicon carbide.

It is a further object of the present invention to convert the pollutant by-product waste gases into useful products.

It is a further object of the present invention to provide a system for converting the pollutant by-product waste gases which is economical and energy efficient.

In order to achieve the above objects, in accordance with the present invention there is provided a continuous flow method and system of converting environmentally pollutant by-product waste gases emitted during the manufacture of a product in a first manufacturing plant to a useful product in a second plant such that release of the gases into the atmosphere may be prevented. More particularly, there is provided a method which comprises:

providing a methanol manufacturing plant in which the by-product gases are usable in the manufacture of methanol;

continuously flowing the by-product gases as emitted from the first manufacturing plant directly to the methanol manufacturing plant for immediate processing in the manufacture of methanol; and immediately processing the by-product gases at the methanol manufacturing plant in the manufacture of methanol such that evolution of the pollutant by-product waste gases into the atmosphere may be prevented.

Still more particularly, the present invention provides a continuous flow method and system of converting environmentally pollutant by-product waste gases emitted during the manufacture of silicon carbide in a silicon carbide manufacturing plant comprising:

providing a methanol manufacturing plant in which the by-product gases are usable in the manufacture of methanol;

continuously flowing the by-product waste gases as emitted at the silicon carbide manufacturing plant to the methanol manufacturing plant; and immediately processing the by-product gases in the manufacture of methanol such that evolution of the by-product waste gases into the atmosphere may be prevented.

DETAILED DESCRIPTION OF THE PREFERRED EMBODIMENTS

The term "continuous flow", as used herein, refers to the substantially uninterrupted flow of by-product gases, as emitted during the manufacture of a product at a first manufacturing plant, from the first manufacturing plant to a second manufacturing plant. This is in contrast to a process which includes storing the by-product gases such as in containers while awaiting their being directed to the second manufacturing plant for use in the production of a product. By-product gases from production of silicon carbide have typically been "collected" i.e., brought together at each furnace before being immediately routed from the furnace for incineration. Such a collection process should not be construed as "storage" of the gases. Neither should the flow of the gases through manholes for cleansing thereof, as described hereinafter, be construed as "storage". The term "as emitted", as used herein, with reference to the by-product gases, refers to the by-product gases as produced from the manufacture of the product at the first manufacturing plant including collection or bringing together of the gases for immediate flow toward the second manufacturing plant.

Figure 1:
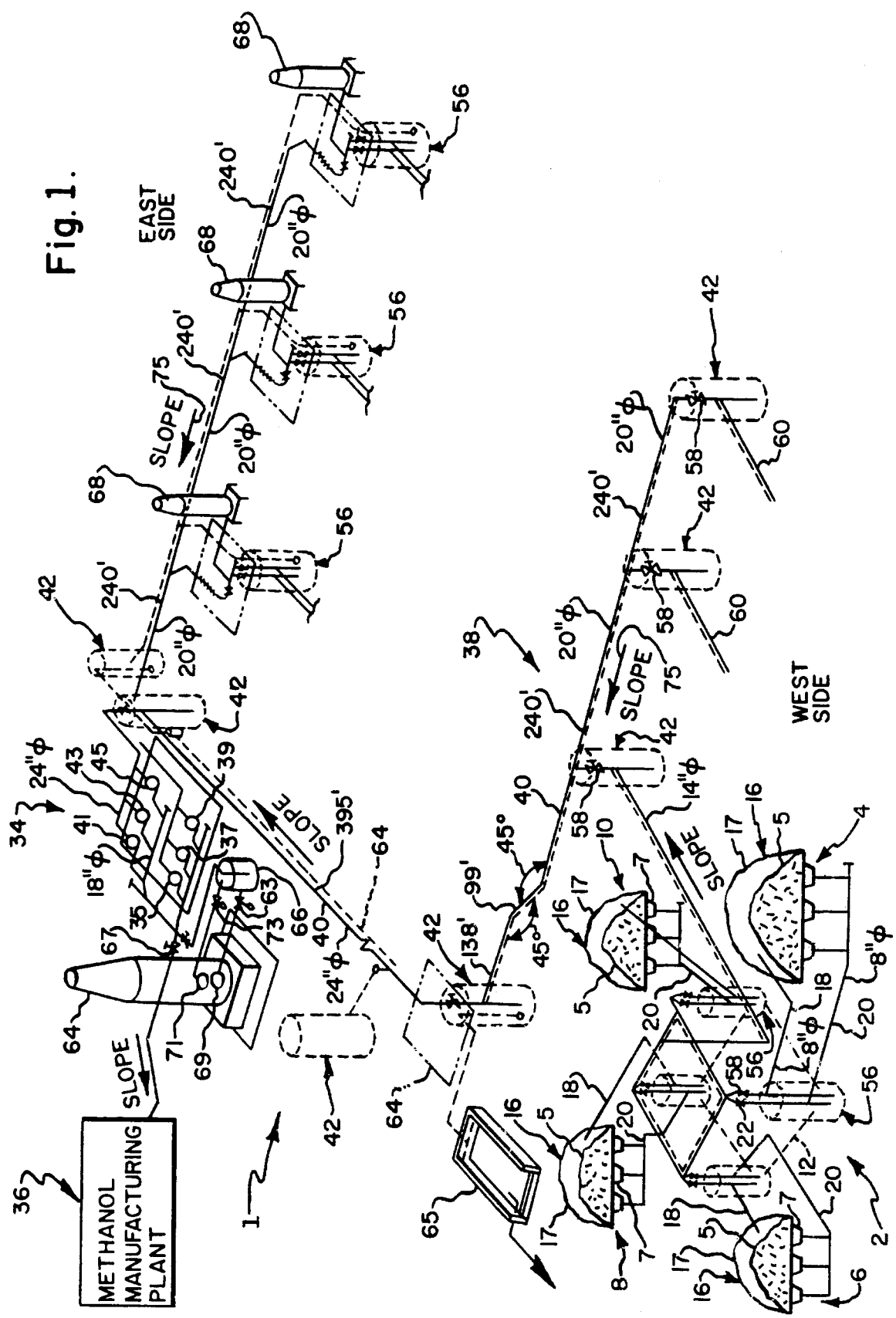
FIG. 1 discloses a schematic view of a system according to the present invention.
Figure 2:
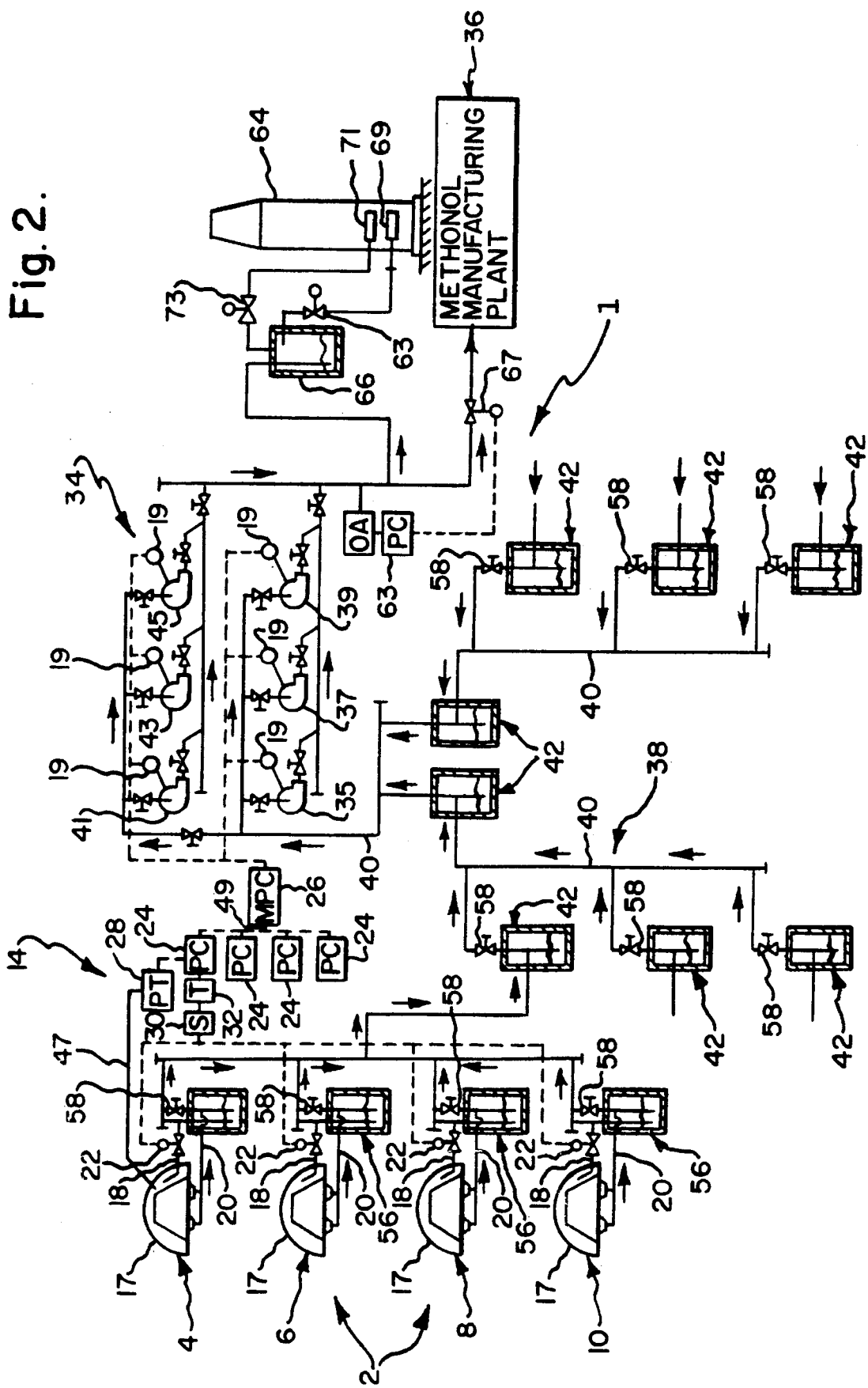
FIG. 2 discloses a schematic view of the control system thereof.

With reference to FIGS. 1 and 2, there is illustrated a continuous flow method of converting environmentally pollutant by-product gases, such as carbon monoxide and hydrogen sulfide, emitted in a silicon carbide manufacturing plant, generally indicated at 1, during the manufacture of silicon carbide. The silicon carbide is manufactured at silicon carbide manufacturing plant 1 from a mixture of silica sand and carbonaceous materials. The basic reaction for the manufacture of silicon carbide is:

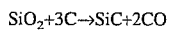

$$SiO_2 + 3C \rightarrow SiC + 2CO$$

The silicon carbide is prepared according to a batch or discontinuous process in a furnace generally shown in FIGS. 1 and 2. With reference to FIG. 1, the silicon carbide manufacturing plant 1 includes a plurality of furnace groups, one such group generally shown at 2, which provide outputs respectively through lines 60. Although, for ease of understanding, only one such furnace group 2 is shown, it should be understood that the others are similar. Typically, each furnace group 2 includes four furnaces 4, 6, 8 and 10. Each furnace group includes one transformer building 12 per group of four furnaces. The transformer building 12 conventionally includes a transformer (not shown), capacitor (not shown), pump (not shown) and control system, generally indicated 14 in FIG. 2, for operating the furnaces in each furnace group. The furnaces 4, 6, 8 and 10 are typical of the furnaces in the other furnace groups and are batch or discontinuous flow furnaces. During operation, the furnaces are staggered to provide continuous production of silicon carbide. For example, the silicon carbide manufacturing plant 1 shown in FIG. 1 includes six furnace groups wherein one furnace within each group is running at any given time of plant operation. When a furnace running within each group shuts down another furnace in that group starts or will have begun running. Such operation of the furnaces may be regulated using principles commonly known to those of ordinary skill in the art to which this invention pertains.

Except for the furnaces 4, 6, 8 and 10 preferably being batch furnaces, the particular construction of the furnaces forms no part of the present invention. The furnaces may be of any suitable construction such as, for example, of the electrical resistance type disclosed in U.S. Pat. Nos. 3,989,883, 3,950,602 and 4,158,744, the disclosures of which are hereby incorporated by reference. In the electrical resistance furnace the electric current effects a resistance heating. In making silicon carbides, a diffusion reaction develops within the temperature range of from about 1500° C. to 2500° C., preferably from about 1700° C. to 2500° C. Silicon carbide sublimes, rather than melts, under normal pressure, and it dissociates at temperatures above 2500° C. This requires that this reaction be carried out by direct electrical heating according to the resistance principle in an electrical resistance furnace, rather than by heating in an arc furnace. The present invention is only concerned with the disposition or use made of the gases no matter how they are produced though preferably in batch furnaces the operation of which is staggered to achieve uniform continuous flow.

The basic reaction at silicon manufacturing plant 1 for the manufacture of silicon carbide, the composition of the reactants silicon dioxide and coke (carbon) and the product silicon carbide are shown in Table I.

TABLE I

SiC Production

A. Reaction: $SiO_2 + 3C \rightarrow SiC + 2CO$—Theoretical
   Volumes: 55% + 45% — 40 + 56—Units - Lbs., Tons, etc.
B. Quality:
   I. Reactants:

| | | |
|---|---|---|
| 1. $SiO_2$ | $SiO_2$ | 99.4% |
| | balance | = $FeO_3$ CaO, etc. |
| 2. Coke | C | = 80–83% |
| | $S_2$ | = 5.5% max. |
| | Volatiles | = 10% + 2 (Aromatics) |
| | Ash | = 0.5% max. |
| | Moisture | = 10% max. |
| II. Products | | |
| 1. SiC (97%) | SiC | = 97% +/− 1% |
| | S2 | = Trace |
| | Free $SiO_2$ | = 0.5% max. |
| | Free C | = 0.75% max. |
| | Al, Fe, etc. | = 0.5% max. |
| 2. SiC (90%) | SiC | = 90% +/− 2% |
| | S2 | = 0.2% max. |
| | Free C | = 3.0% + 1 |
| | $SiO_2$ | = 3.0% + 1 |
| | CaO, MgO, etc. | = balance. |

Various environmentally pollutant by-product gases, particularly carbon monoxide, carbon dioxide, and hydrogen, are produced as a result of the reaction shown in Table I. In addition, other by-product gases produced include other gaseous compounds such as hydrocarbons, in particular, methane and hydrogen sulfide which are formed from the impurities of the coke used. The gas production and composition from the manufacture of silicon carbide for the silicon carbide manufacturing plant described herein, assuming a four furnace operation, 25,000MWh/mo average power consumption and 300 cu m/MWh (10,593 cu ft/MWh) is shown in Table II.

TABLE II

GAS DATA

I. Gas Production:

| | |
|---|---|
| Volume/mo (standard). | $7.4 \times 10^6$ cu m = $261 \times 10^6$ cu ft. |
| Volume/yr = (standard). | $88.8 \times 10^6$ cu m = $3,135 \times 10^9$ cu ft. |
| Daily Max. - | $11.7 \times 10^6$ cu ft. |
| Daily Min. - | Practically 0 possible, if prolonged curtailment occurs, over 24 hours. |

II. Gas Composition, Average

| | | |
|---|---|---|
| CO | - | 46.72% |
| $H_2$ | - | 33.55% |
| $CO_2$ | - | 12.57% |
| $CH_4$ | - | 3.29% |
| $N_2$ | - | 1.74% |
| $O_2$ | - | 0.16% |
| $H_2S$ | - | 1.81% |

The by-product gases as emitted during the manufacture of silicon carbide are collected by a collector apparatus, generally indicated 16, associated with the furnaces. The collector apparatus 16 is characterized by arranging beneath a ballast 5 with the resistance core embedded therein, a bed filled with porous material (not shown), and/or the base and the slopes of the bed may be suitably sealed with a gas-impervious layer, i.e., flat cover 17 above the ballast. Within the bed and beneath the cover, gas outlet ducts 18, 20 are installed through which the by-product gas collected are removed from the furnaces. The bed is arranged beneath the ballast 5 and preferably below the furnace bottom and advantageously extends through the length of the furnace between the electrodes 7. The cross-sectional configuration for this bed is not limited to any particular configuration. The seal 17 can be made, for example, of a concrete layer of a synthetic material that is situated at a suitable distance from the hot burden. For filling the bed, a heat resistant solid material having a porous or granular structure such as pumice, grit, granulated pumice, concrete gravel, sand, or quartz grit and preferably a sandstone (silica rock) may be provided for filling the bed.

The flat cover or sheet 17 disposed above ballast 5 also extends advantageously over the length of the furnace. When using an adequately high ballast if care is taken that the surface is no longer sufficiently hot to damage the cover 17, or to destroy it, the cover 17 may suitably be a material not absolutely heat resistant such as gas-impervious sheets, impregnatated fabrics, or canvas covers. The material preferably comprises polyethylene sheets having a thickness of from about 0.1 to about 0.5 millimeters and preferably about 0.3 millimeters. The flat cover 17 may advantageously be used with furnace installations of the electrical resistance type having bottom electrode arrangements 7 which are operated as open mound furnaces without walls. In such installations, the whole charge cone can be covered up to the ground level without the danger of the covering material coming into contact with hot parts of the furnace.

Gas outlet ducts 18, 20 are suitable pipes placed within the porous bed of material in the furnace and beneath the cover and are provided with side openings (not shown) in the part of the pipes which project into the porous bed and/or under the cover to receive the by-product gases as emitted during the manufacturing process. Gas outlet ducts 18, 20 may be constructed of iron or synthetic material that can be perforated or provided with slots within the furnace. The number and cross section of the pipes arranged within the porous bed and/or beneath the cover depends on the size of the furnace and on the electric charge provided which regulates the amount of by-product gases expected. With reference to FIG. 2, overgas outlet duct 18, and undergas outlet duct 20 extend from above and below the furnace, respectively. Overgas outlet duct 18 connects to modulating valve 22. Modulating valve 22 is controlled by a suitable process controller 24 which receives a pressure signal through line 47 from a suitable pressure transmitter 28 of the pressure under cover 17 to open and close modulating valve 22 so as to regulate the gas pressure under cover 17 such that the cover constitutes an air supported structure. Each furnace group has its own process controller 24 that controls the modulating valve associated with that furnace. Undergas outlet duct 20 connects to hand valve 58 which is pre-set manually to the desired vacuum pressure.

For a more complete interface between the silicon carbide plant and the methanol plant additional controls may be implemented. For purposes of illustration and, not limitation, the process controller 24 from each furnace group may provide feedback to a suitable main process controller 26 for each furnace group on the status of the operating conditions of the one furnace per group that is operating. The process controller 24 compares the pressure signal to the valve position, as determined from a signal potentiometer (not shown) within modulating valve 22, and suitably opens or closes the valve 22 to control the gas pressure under the cover. This process occurs at each furnace group simultaneously for the one furnace per each group that is operating at any one time. A four way selector switch 30 to select currently operating furnaces and a timer switch 32 to prevent over reaction of modulating valve 22 are also provided.

The main process controller 26 would provide a secondary level of process control for maintaining the pressure under cover 17. Process controllers 24 would provide signals to the main process controller 26 through lines 49 when predetermined maximum operating pressures are exceeded beneath the cover 17 and the modulating valve 22 is accordingly fully opened. When this condition occurs, the main process controller 26 would automatically start a blower fan motor, generally indicated 34, for added control capacity of the flow of the by-product gas. The blower fans are described hereinafter in greater detail. For self support of cover 17 a pressure differential in the order of 6 to 12 mm $H_2O$ (millimeter water column) may typically be sufficient. The minimum pressure required for self support of cover 17 depends upon the properties of the material used for the cover. For example, when using a polyethylene sheet having a thickness of about 0.2 mm, a pressure differential of about 10 mm $H_2O$ may be sufficient for supporting the cover under normal conditions. By "normal conditions" is understood to be an ambient air pressure of 760 mm Hg (10 mH2O) predominating outside the cover with no disturbing winds. When the external or ambient pressure conditions changey for example, due to the effect of the weather and especially due to the velocity of the winds, the pressure differential should be suitably modified in accordance with principles commonly known to those of ordinary skill in the art to which this invention pertains, to prevent the flexible cover from being either torn away by the gusts that suddenly appear or from frictionally contacting the ballast surface that contains sharp edged waste materials. Firm retention of the cover over the furnace may additionally be insured by piling mix material on its closing edges. For a more detailed description of the collector apparatus described hereinabove, reference is made to U.S. Pat. No. 3,976,829, the disclosure of which is hereby incorporated by reference.

Figures 5, 6:
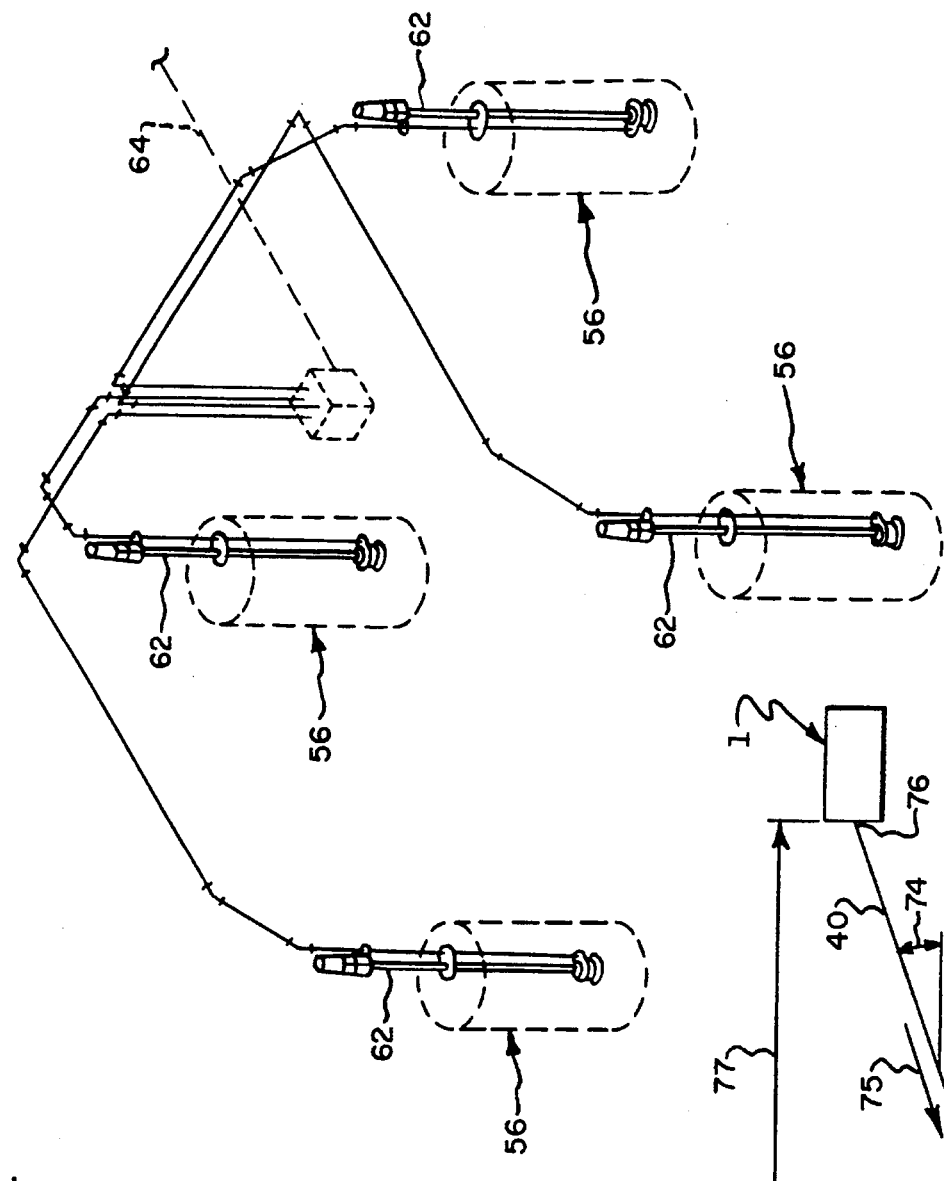
FIG. 5 discloses a schematic view of a sump pump system associated with the manholes illustrated in FIG. 4.
FIG. 6 discloses a simplified elevation schematic view of the system of FIG. 1 illustrating the slope of the pipelines between first and second plants.

The by-product gases are collected in collector apparatus 17 during the manufacture of silicon carbide in the furnaces. Thereafter, the pollutant by-product gases are continuously flowed through piping 40 from the silicon carbide manufacturing plant 1 to a methanol manufacturing plant, generally indicated 36, for immediate processing in the manufacture of methanol to thereby advantageously eliminate costly intervening storage steps of the gas while preventing evolution of the pollutant by-product waste gas into the atmosphere. The methanol manufacturing plant 36 is therefore preferably located in proximity to the silicon carbide manufacturing plant 1, i.e., sufficiently close, for example, a distance, illustrated at 77 in FIG. 6, therebetween which is less than about 1 mile apart so as to not be unduly expensive to build and operate. The methanol manufacturing plant 36 may be a conventional high pressure or low pressure manufacturing plant, and more preferably is a high pressure plant. The by-product gases are processed in methanol manufacturing plant 36 into methanol and sulfur. The production process used for producing the methanol and sulfur consists of technology currently available and known to those of ordinary skill in the art to which this invention pertains. Thus, the particular type of methanol production plant forms no part of the present invention and therefore need not be described further.

The first step in the processing of the by-product gases at the methanol manufacturing plant for production of methanol and sulfur is compressing up to the methanol reaction pressure the by-product gases which consist mainly of hydrogen, and carbon monoxide. The next step is the desulfurization of the by-product gases using a sulfur removal system (not shown). The sulfur removal system may consist of any currently available system capable of removing sulfur from gases. One type is the wet process which involves scrubbing the gases by contact with organic or aqueous solutions of alkaline chemicals to extract the acid sulfur compounds by either physical or chemical reactions between components of the gases and liquids. The reactive chemicals utilized in these processes include ammonia, organic amines, oxides, and carbonates and sulfites of alkali and alkaline earth metals. Another type of process which may be utilized involves contacting the gases with dry solid sorbents. A process of this type utilizes the physical properties of sorbents such as activated alumina, activated carbon and silicon gel and operate at low temperatures. Alternatively, this type of process may utilize minerals and chemicals such as dolomite, magnesite, calcite, siderite, magnetite, hematite, bauxite, lime, soda ash and/or magnesia, as solid sorbents containing components that react chemically with sulfur compounds in the gas and operate at relatively high temperatures. Further suitable processes for the desulfurization of the gases involve cooling the hot gas and desulfurizing the cooled gas by contact with agueous solutions of alkaline chemicals. These processes utilize heat exchange eguipment of alloy construction. Desulfurization of the gases by contact with minerals or chemicals at high temperatures is another proposed process which may be utilized and involves the use of limestone or dolomite as a sorbent for the sulfur whereby chemical reactions between calcium and the minerals and sulfur in the gas occur which provide calcium sulfide and calcium sulfate in the reactive solids thereby removing the sulfur from the sulfur bearing gases. For purposes of illustration and not limitation, a more detailed desulfurization process which may be utilized in accordance with the system of the present invention is disclosed in U.S. Pat. No. 4,061,716, the disclosure of which is hereby incorporated by reference. The sulfur removed from the by-product gases is thereafter collected and sold. Thus, evolution of the sulfur into the atmosphere is prevented, as is increasingly demanded by the public for health and environmental reasons.

After the sulfur removal step, the remaining by-product gases, which consists mainly of hydrogen and carbon monoxide, are mixed with natural gas, which is mostly methane, to provide a constant flow rate and a correct carbon balance for processing the gas into methanol. The amount of natural gas mixed with the by-product gas is dependent upon the volume of by-product gas supplied to the methanol manufacturing plant from the silicon carbide manufacturing plant. Thus, as the amount of by-product gas is increased, the amount of natural gas may be decreased. In processing the gases into methanol, perhaps 75% of the feedstock will initially be natural gas with the remaining 25% being the by-product gases produced from the manufacturer of silicon carbide. As the silicon carbide manufacturing plant increases its capacity and thereby produces larger amounts of by-product gases, the amount of natural gas may be decreased as a percentage of the feedstock used in the production of methanol.

The next step in the production of methanol is reformation of the feedstock gases which now consist mainly of hydrogen, carbon monoxide, methane and water. Reformation shifts the oxygen to the carbon to form more carbon monoxide. The basic reaction for the reformation of the feedstock gases is:

$$CH_4 + H_2O \rightarrow CO + 3H_2$$

The reformation process is controlled to provide a balance of one part carbon monoxide to two parts of hydrogen. This process in the methanol manufacturing industry is known as steam reforming.

The synthetic gas (CO+2H2) formed as a result of the reformation step is then compressed. Thereafter, reaction of the synthetic gas (CO+2H2) to form methanol (CH$_3$OH) is carried out. The reaction of converting the synthetic gas to form methanol may be accomplished by means of equipment known as a "synthetic-loop", designed and manufactured by Lurgi Kohle & Mineraloltechnik GmbH.

The last step in the methanol production process is purifying any unwanted compounds or material which are formed or present after the synthetic gas is converted to methanol. The purification process is accomplished using a standard distillation system. After purification, the methanol is stored for sale to third parties.

Methanol is used primarily as a chemical feedstock to produce formaldehyde, acetic acid and in the manufacturer of MTBE, a fuel additive. The use of methanol as a chemical feedstock represents approximately 70% of the total demand for methanol. In general, the market price of methanol follows the price of crude oil. The marketprice of methanol has been subject to substantial fluctuations during the late 1980's, ranging from a low of about $0.26 per gallon to a high of about $0.64 per gallon. As a result of numerous world scale production facilities becoming operational, the worldwide productive capacity of methanol increased from 13,960,000 metric tons to 22,798,000 metric tons. According to the 1988 *Methanol Annual* (the "Crocco Report") prepared by Crocco and Associates, Inc., the demand for methanol in the United States market is expected to increase at an average annual rate of 4.75% during the early 1990's. During that same time period, however, the production of methanol was projected to remain fairly constant in that it was not expected that any world scale production facilities would be constructed, As a result, the Crocco Report projects that the demand for methanol may exceed the supply by 1991. In this connection, a system of the present invention may typically have the capacity to produce at least 250 tons per day of methanol and 7 tons per day of sulfur. As a result, methanol may be produced in accordance with the present system to substantially decrease the projected shortage of the supply of methanol. Further, by converting the by-product gases into useful products, such as sulfur and methanol, emission of pollutant gases in the amount of about 7 tons sulfur and 12 million cubic feet of by-product waste gas daily per single silicon carbide plant into the atmosphere may be eliminated. A methanol manufacturing plant as described herein may perhaps utilize approximately seven million standard cubic feet per day of natural gas as feedstock for the production of methanol. Further, perhaps 4.4 billion cubic feet or more of by-product gases per year may typically be continuously flowed from a silicon carbide manufacturing plant to a methanol manufacturing plant.

Means, generally indicated at 38, for continuously flowing the by-product gases as emitted from silicon carbide manufacturing plant 1 directly to methanol manufacturing plant 36 for immediate processing in the manufacturing of methanol and sulfur comprises a gas routing and condensation drainage system. The gas routing and condensation drainage system 38 includes piping lines 40 for continuously flowing the by-product gases to methanol manufacturing plant 36 and manholes, generally indicated at 42, associated with piping lines 40 for receiving sludge and water condensation that drops-out from the by-product gas as it is flowed from silicon carbide manufacturing plant 1 to methanol manufacturing plant 36. Piping lines 40 of the present system are preferably sized sufficiently for receiving the gases at maximum flow output conditions from silicon carbide manufacturing plant 1 so that friction of the flowing gas in pipe lines 40 is minimized. The size of piping lines 40, is suitably related to the composition of the constituents in the by-product gas. Therefore, it is understood that the size of the piping lines 40 in accordance with the present invention would vary from plant to plant, being dependent on the composition of the by-product gas as well as expected maximum flow rates.

The by-product gas may be analyzed using conventional gas chromatography apparatus to obtain a weight percent of each of the constituents therein. The data for the analysis of the by-product gas from an exemplary furnace as described herein and over a total of 3,925 observations, may be shown as in Table 3.

TABLE 3

GAS FLOW STATISTICS FOR ONE FURNACE

|  | MINIMUM | MAXIMUM | AVERAGE |
|---|---|---|---|
| PERCENT CO2 (1) | 9.57 | 15.57 | 12.57 |
| PERCENT H2 (1) | 28.55 | 38.55 | 33.55 |
| PERCENT O2 (1) | 0 | 1.66 | 0.16 |
| PERCENT H2S (1) | 0.25 | 3.31 | 1.81 |
| PERCENT N2 (1) | .24 | 3.24 | 1.74 |
| PERCENT CH4 (1) | 1.79 | 4.79 | 3.29 |
| PERCENT CO (1) | 41.72 | 51.72 | 46.72 |
| GAS FLOW A.C.F.M. (4) | 200 | 4064 | 2451 |
| GAS FLOW S.C.F.M. (4) | 157 | 3430 | 2101 |
| PERCENT H2O (2) | 1.56 | 68.73 | 24.06 |

TOTAL GAS DATA
(FOUR FURNACES ON LINE)

|  | MAXIMUM | AVERAGE |
|---|---|---|
| GAS FLOW A.C.F.M. | 16,256 | 9,780 |
| GAS FLOW S.C.F.M. | 13,656 | 8,800 |
| TEMPERATURE (DEG. C.) | 84 | 57.6 |
| B.T.U. CONTENT (BTU/CU. FT.) | 338.6 | 282.3 |

NOTES:
(1) PERCENT OF DRY GAS.
(2) PERCENT OF WET GAS.
(3) PEAKS INDICATE AIR LEAK.
(4) DRY GAS FLOW.

The maximum Actual Cubic Feet per Minute gas flow, which in this example is 16,256, may then be used to size the piping lines. This number indicates the highest by-product gas at maximum flow per furnace. The pipe sizing formula which may be utilized for sizing pipelines 40 for gases, provided by Cameron Hydrolic Data, Ingersoll-Rand Company, is shown in Table 4.

TABLE 4

$$R = \frac{Dvp}{u} = \frac{22{,}735Qp}{dz} = \frac{378.9q_1p}{dz} = \frac{6.32W}{dz}$$

TABLE 4-continued $$P = \frac{fLv^2p}{24gd} = \frac{43.53fLQ^2p}{d^5} = \frac{.01209fLq^2p^2}{d^5} = \frac{.00000336fLW^2}{pd^5}$$

d = inside diameter of circular pipe (inches)
f = friction factor, dimensionless
g = acceleration of gravity (32.174 ft/sec$^2$)
L = Length of pipeline, including equivalent length for loss through fittings (feet). Note: In long lines over about 4,000 feet where loss due to fittings is a small portion of the total they can usually be neglected.
p = density at temperature and pressure at which fluid is flowing (16 per ft.3)
q1 = flow of gas (cv ft. per min. at temperature and pressure of flow conditions)
Q = Flow of gas 1 cu. ft. per second at temperature and pressure of flow conditions).

In accordance with the formula, the diameter of piping lines 40 may range from a minumum of an eight inch diameter to a maximum of a thirty inch diameter as the piping lines extend from silicon carbide manufacturing plant 1 to methanol manufacturing plant 36. The pipe having a diameter less than twelve inches may be composed of standard A53 schedule 40 low carbon steel. The pipe having a diameter greater than twelve inches may be composed of standard A-53 three-eighths inch wall thickness low-carbon steel pipe. The valves and fittings used in piping lines 40 may be standard 150 pound valves and fittings. Values for determining the pipe lengths in connection with the elbows, tees, bends and the various types of valves may be determined using principles commonly known to those of ordinary skill in the out to which this invention pertains.

The diameters and lengths of piping lines 40 are preferably selected for maximum flow output conditions by inputting the various data including values of friction of fluids in a pipe into a computer program. An illustrative computer program for determining the diameters of the piping lines (East and West side) is set forth in the attached listing as Exhibit A and B for East side and West side respectively, East and West sides referring to two different sides of a plant, as shown in FIG. 1. The programs are written in d-Base language, and were developed by Exolon ESK Corporation of Hennipen, Ill. for use with sizing the piping lines of the present system. Other computer programs can of course be employed for sizing the piping, for example, one such commercially available program is known as Flow V 2.0. Another sizing consideration taken into account is correction for suction and temperature. Fan manufacturers use air at standard conditions (70° F. and 0.075 LBs/ft$^3$) to rate the performance of their equipment. When resistance is placed on the fan inlet, the suction of the fan creates a partial vacuum at the inlet. The partial vacuum lowers the density of the gas at the inlet. Since fans are rated with 0.075 density at the inlet correction may be required to make the proper selection, which may be determined in accordance with the following formula:

$$d = .075 \times \frac{530}{460 + T} \times \frac{BP}{29.92} \times \frac{AiP}{AP} \times SG$$

d = actual density at fan inlet
T = Temperature of (dry bulb) at inlet
BP = Barometric Pressure, "Hg"
AiP = Absolute Pressure at fan inlet
AP = Absolute Pressure
SG = Specific Gravity of the Gas For purposes of illustration and, not limitation, and with reference to FIG. 1, there is shown the diameters and lengths as determined using the values in the above tables for the piping lines of the illustrated system in accordance with the present invention. It is understood that piping diameter and lengths are dependent upon the particular system and values used in the sizing formulas.

It is desirable to remove as much sludge, i.e., furnace residue and particulate matter, as possible in order to provide a sufficiently clean gas for use as feed stock in the production of methanol. As the by-product gas flows through pipe lines 40 from silicon carbide manufacturing plant 1 to methanol manufacturing plant 36, a cooling effect on the gas occurs. This cooling effect, facilitated by the slope of the pipe 40 and sizing thereof as hereinbefore discussed, causes sludge and water condensate to drop out of the by-product gas to thereby cleanse it. But practical considerations, namely geographical, may limit the amount of slope achievable.

It is desirable that the piping lines stay clean of sludge and water condensate because if sludge builds-up in the line, in addition to clogging, the inside pipe diameter will decrease which will increase the velocity of the gas through the pipe such that less cooling effect will be apparent giving a dirtier gas. The slope, illustrated at 74 in FIG. 6, of the piping lines 40 is preferably at least about 1% downwardly in the direction of gas flow from the first plant 1 to the second plant 36, as indicated by arrows 75 in FIGS. 1, 2, and 6, and for a distance, preferably over the entire distance, length and geographic conditions permitting, between the plants 1 and 36, sufficient to prevent clogging of the system as well as provide a relatively cleansed gas free of furnace residue and particulate matter sufficient for use in plant 36, for example, over a distance of about a mile. The portion of gas flow piping within plant 1 may, of course, also be similarly sloped, as illustrated at 75 in FIG. 1. In order to prevent clogging problems from sludge drop-out, any time there is a change in elevation a suitable manhole, generally indicated at 42, is preferably provided to collect the sludge and water condensate that drop-out from the by-product gas due to the cooling effect because of velocity and direction changes as the gas moves through piping lines 40.

The more manholes utilized in the present system, within practical considerations, the better cleansed the final by-product gas will be and the less likelihood of sludge build-up and eventual clogging in the piping line system itself. Examples of suitable manholes which may be utilized in the present system include either six foot diameter manholes of standard pre-cast manhole sections produced by Eller and Wiley Block Company of Dixson, Ill. or standard pre-cast manhole sections greater than six foot diameter produced by Material Service Company of Chicago.

With reference to FIGS. 1 and 2, a manhole 42 is provided in the piping between the plants 1 and 36 preferably, at each change in elevation of the piping. It is therefore understood that the positioning and numbering of the manholes will vary. For example, the positioning of piping lines 40 and manholes 42 may differ on opposite sides of a plant due to geographical considerations.

Figure 3:
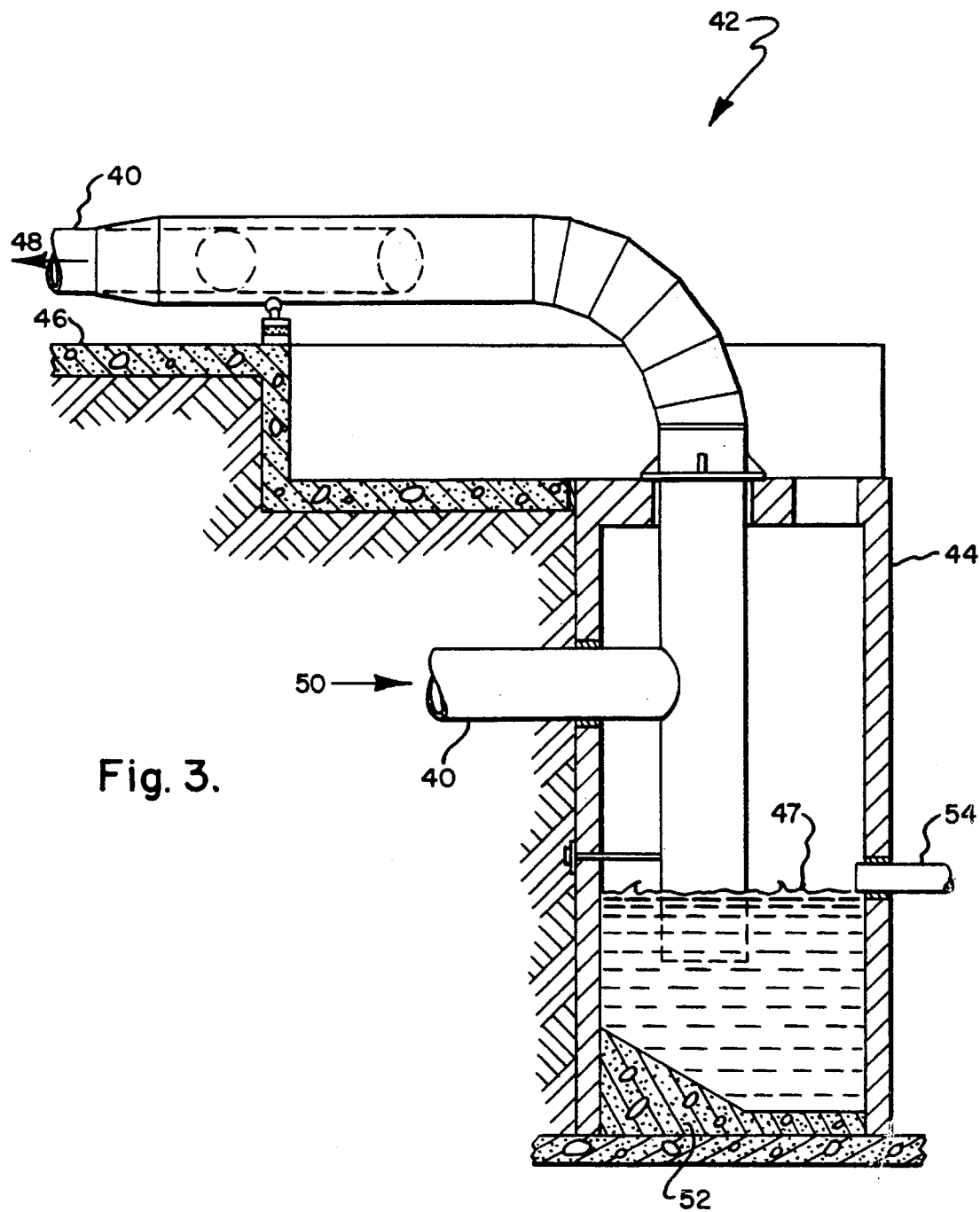
FIG. 3 discloses a side view of a manhole used in the system.

With reference to FIG. 3, there is shown a typical manhole 42. The manhole 42 is comprised of a pre-cast manhole section 44 which is positioned beneath the ground 46 in order to most effectively achieve drop-out of particulate as the gas rises. The by-product gas generally enters the manhole 42 at a lower end thereof through piping line 40 as shown by arrow 50 and generally exits the manhole at a position above where it entered such as at the top thereof through piping line 40, as shown by arrow 48. Each manhole further contains a water seal 47 to maintain the system under vacuum and prevent air from entering the system and possibly causing an explosion. As a result of the change in elevation and the cooling effect on the by-product gases, sludge and water condensate 52 drop out of the by-product gas and are collected at the bottom of manhole 42. Drainage pipe 54 is provided to remove the sludge and condensate water from the manhole 42.

Figure 4:
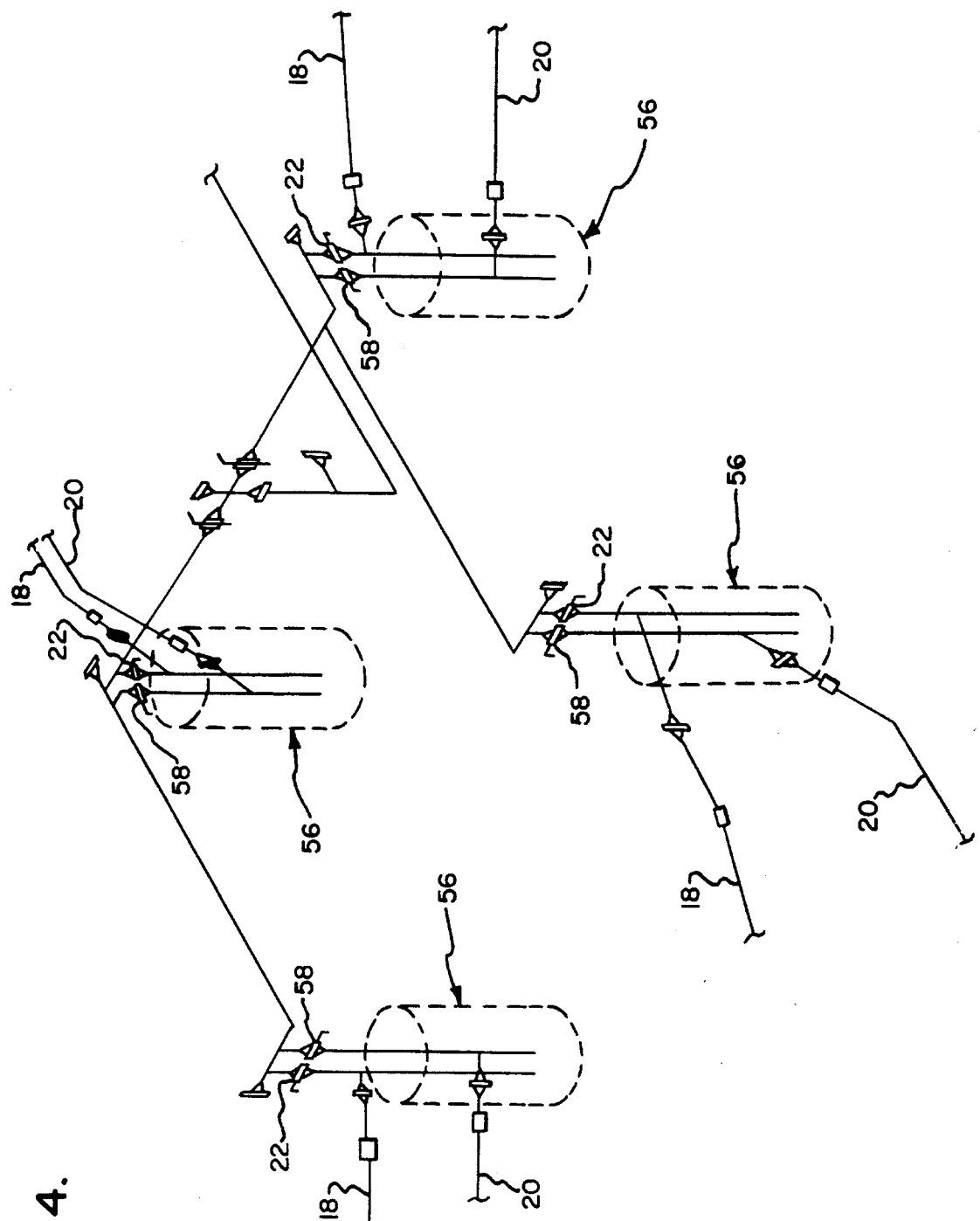
FIG. 4 discloses a schematic view of manholes of the system which are associated with each furnace in a furnace group.

Furthermore, and with reference to FIG. 4, each furnace per furnace group in the silicon carbide manufacturing plant includes a manhole 56 to which the by-product gas is first flowed upon emission from the furnace. By-product gases flow through overgas outlet duct 18 and undergas outlet duct 20 directly from the silicon carbide furnace to manhole 56. The overgas is regulated out of manhole 56 through modulating valve 22 and the undergas is regulated out of manhole 56 through manually regulated valve 58. The by-product gases are then combined into a single pipe line 60 for flow to the main piping lines 40 where all the by-product gases produced from each of the furnace groups are combined for flow to the methanol manufacturing plant.

With reference to FIG. 1, a suitable water treatment lagoon system which transports the water condensate that drops from the by-product gas for treating and recycling of the water is also provided. The transport system is indicated by segmented lines 64 which transport the water to filter bed 65 for subsequent transportation to the water treatment lagoon (not shown). The water treatment lagoon system is conventional in nature and any known system may be utilized in accordance with the present invention. For example, with reference to FIG. 5, each manhole 56 in the system may comprise a suitable sump pump 62, such as a longshaft pump for 180° water use, supplied by Tramco. The sump pump 62 pumps out the water from the manholes to the filter bed 65 for subsequent transport and treatment at the lagoon system (not shown). Alternatively, the furnace group may include lines associated with the manholes which flows the water therefrom by gravity to a downward sloping tile through which transports the water to the lagoon system for treatment. The sludge remaining in manholes 42 and 56 is periodically removed from the manholes and appropriately disposed of. Thus, water condensate in manholes 42 may be drained periodically through pipe 54 or pumped by the sump pump for removal. It is understood that the manhole system utilized in the present invention to collect the sludge and condensate water drop-out, is for purposes of illustration only, and not limitation. It is within the scope of the present invention to employ any conventional filter system which would remove the sludge and condensate water and reduce clogging of the system.

With reference to FIGS. 1 and 2, a plurality of high temperature, radial, heavy duty blower fans, generally indicated 34, are provided to regulate the flow rate of the by-product gases from silicon carbide manufacturing plant 1 to the methanol manufacturing plant 36. Six blower fans 35, 37, 39 in parallel and 41, 43, 45 in parallel are balanced and manually regulated as determined by the amount of by-produce gas produced. As previously mentioned, if a main process controller 26 (FIG. 2) is provided, the fans could be automatically regulated on and off by the main process controller 26 in accordance with desired gas flow. The maximum gas flow is dependent on fan capacity. Also, a suitable computer program, which may be developed using principles commonly known to those of ordinary skill in the art to which this invention pertains, may be used to coordinate and balance the fans to maximize flow rate of the by-product gases. The flow rate of the by-product gases is determinative of the diameter of the piping which may be selected based on the capacity of the blower fans used taking into account the friction factor of the flowing gases. A suitable fan is marketed by VEN TAPP GmbH of Germany, and may have a volume of 8,000 m₃/h and pressure of 100 to 134 mbar. Each blower fan is operated by a conventional motor 19 and comprises a manually operated valve for isolating the fan. It is understood that one large blower fan, having a speed adjustment control for regulating the fan in accordance with changes in by-product gas flow, may be substituted herein for the plurality of small blower fans.

The by-product gas is continuously flowed through the piping lines by regulating the capacity of the blower fans to accommodate the gas output from the furnaces at any given time. As previously mentioned, the blower fans are manually regulated and/or may be regulated by a main processing controller in response pressure and flow requirements. If the volume of the by-product gas being flowed is such that it is higher than the volume necessary at any one time during the methanol production, excess by-product gas is directed to pilot burner 69 at incinerator 64 by process controller 63 opening and closing modulating valve 65. Routing of the by-product gas to the methanol plant 36 is through modulating valve 67 which is also controlled by process controller 63. If shutdown occurs at the methanol manufacturing plant, for example due to maintenance, all gas is flowed to a main burner 71 at incinerator 64 through modulating valve 73. The incinerator may typically have a capacity to incinerate a gas flow volume of 15,000 S.C.F.M. The by-product gas flow which is diverted to either of the burners 69 or 71 of incinerator 64 is flowed through a water seal pot 66 to prevent flames during the incineration process from coming back into the system and potentially causing an explosion. Water seal pot 66 functions similarly as the water seal in the manholes. Additionally, each furnace group may comprise a backup incinerator 68.

It is to be understood that the invention is by no means limited to the specific embodiments which have been illustrated and described herein and that various modifications thereof may indeed be made which come within the scope of the present invention as defined by the appended claims. For example, the carbon and hydrogen elements of the by-product gases could be converted into acetic acid.

We claim:

1. A system comprising:
   an electrical resistance furnace silicon carbide manufacturing plant including a plurality of batch furnaces which emit environmentally pollutant by-product gases during the production of silicon carbide;
   means for staggering the operation of said batch furnaces to provide a continuous flow of the by-product gases from said silicon carbide manufacturing plant;
   a methanol manufacturing plant for processing the by-product gases, for production of methanol; and
   means for continuously flowing the by-product gases as emitted from said silicon carbide manufacturing plant directly to said methanol manufacturing plant for immediate processing for production of methanol whereby evolution of the pollutant by-product gases into the atmosphere may be prevented.

2. The system of claim 1, further comprising means for cleansing the by-product gases as they are continuously flowed from said silicon carbide manufacturing plant to said methanol manufacturing plant.

3. The system of claim 1, wherein said batch electrical resistance furnaces are capable of heating a mixture of coke and silicon dioxide to a temperature within the range of about 1500 to 2500 degrees Centigrade for producing silicon carbide.

4. The system of claim 3, further comprising means for cleansing the by-product gases as they are continuously flowed from said silicon carbide manufacturing plant to said methanol manufacturing plant.

5. The system of claim 1, wherein said continuous flow means comprises a piping system which extends between the silicon carbide plant and the methanol plant for continuously flowing the by-product gases from the silicon carbide plant to the methanol plant.

6. The system of claim 5, wherein said piping system has a slope of at least about 1% over a distance sufficient to cleanse the by-product gas of particulate matter sufficiently for use of the by-product gas in the methanol manufacturing plant.

7. The system of claim 5, further comprising:
   providing at least one manhole at a pipe bend in said piping system for collecting said particulate matter to thereby facilitate cleansing of said system.

8. A system comprising:
   a first manufacturing plant including a plurality of batch electrical resistance furnace means for heating a mixture of coke and silicon dioxide to produce silicon carbide and which emits environmentally pollutant by-product gases including carbon monoxide and hydrogen sulfide during the production of the silicon carbide and including means for staggering the operation of said batch furnace means to provide a continuous flow of the by-product gases from said first manufacturing plant;
   a second manufacturing plant for processing the by-product gases for production of a product; and
   means for continuously flowing the by-product gases as emitted from said first manufacturing plant directly to said second manufacturing plant for immediate processing for production of the product whereby evolution of the pollutant by-product gases into the atmosphere may be prevented.

9. The system of claim 8, wherein said second manufacturing plant is a methanol manufacturing plant.

10. The system of claim 8, wherein said continuous flow means comprises a piping system which extends between said first manufacturing plant and said second manufacturing plant for continuously flowing the by-product gases from said first manufacturing plant to said second manufacturing plant.

11. The system of claim 10, further comprising means for cleansing the by-product gases as they are continuously flowed from said first manufacturing plant to said second manufacturing plant.

12. The system of claim 11, wherein said piping system has a slope of at least about 1% over a distance sufficient to cleanse the by-product gas of particulate matter sufficiently for use of the by-product gas in the second manufacturing plant.

13. The system of claim 11, further comprising:
   providing at least one manhole at a pipe bend in said piping system for collecting the particulate matter to thereby facilitate cleansing of said system.

14. A system comprising:
   a first manufacturing plant which emits environmentally pollutant by-product gases including carbon monoxide and hydrogen sulfide during the production of silicon carbide and which includes a plurality of batch electrical resistance furnace means for producing silicon carbide and means for staggering the operation of said batch furnace means to provide a continuous flow of the by-product gases from said silicon carbide manufacturing plant;

a second manufacturing plant for processing the by-product gases for production of a hydrocarbon product; and means for continuously flowing the by-product gases as emitted from said first manufacturing plant directly to said second manufacturing plant for immediate processing for production of the hydrocarbon product whereby evolution of the pollutant by-product gases into the atmosphere may be prevented.

15. The system of claim 14, wherein said second manufacturing plant is a methanol manufacturing plant.

16. The system of claim 14, wherein said batch furnace means is an electrical resistance furnace capable of heating a mixture of coke and silicon dioxide to a temperature within the range of about 1500 to 2500 degrees Centigrade.

17. The system of claim 14, wherein said continuous flow means comprises a piping system which extends between said first manufacturing plant and said second manufacturing plant for continuously flowing the by-product gases from said first manufacturing plant to said second manufacturing plant.

18. The system of claim 17, further comprising means for cleansing the by-product gases as they are continuously flowed from said first manufacturing plant to said second manufacturing plant.

19. A system comprising:

a first manufacturing plant which emits environmentally pollutant by-product gases including carbon monoxide and hydrogen sulfide during the production of silicon carbide and which includes a plurality of batch electrical resistance furnaces capable of heating a mixture of coke and silicon dioxide to a temperature within the range of about 1500 to 2500 degrees Centigrade for producing silicon carbide and means for staggering operation of said batch furnaces to provide a continuous flow of the by-product gases from said silicon carbide manufacturing plant;

a second manufacturing plant for processing the by-product gases for production of a hydrocarbon product;

piping means for continuously flowing the by-product gases as emitted from said first manufacturing plant directly to said second manufacturing plant for immediate processing for production of the hydrocarbon product whereby evolution of the pollutant by-product gases into the atmosphere may be prevented; and means including means defining at least about a 1% piping means slope for cleansing the by-product gases for use in said second manufacturing plant.

* * * * *